United States Patent
Schoenrock

Patent Number: 5,124,133
Date of Patent: Jun. 23, 1992

[54] APPARATUS AND METHOD FOR PROVIDING A UNIFORM FLOW PROFILE THROUGH LARGE DIAMETER, LOW-PRESSURE VESSELS

[76] Inventor: Wilmer Schoenrock, 10238 S. 1000 West, South Jordan, Utah 84065

[21] Appl. No.: 558,662

[22] Filed: Jul. 26, 1990

Related U.S. Application Data

[63] Continuation-in-part of Ser. No. 267,848, Nov. 7, 1988, abandoned, which is a continuation-in-part of Ser. No. 54,754, May 26, 1987, abandoned, which is a continuation-in-part of Ser. No. 793,213, Oct. 31, 1985, abandoned.

[51] Int. Cl.$^5$ ............................................. B01J 8/02
[52] U.S. Cl. ................................ 422/191; 210/286; 422/188
[58] Field of Search .................... 422/188, 190, 191; 210/286

[56] References Cited

U.S. PATENT DOCUMENTS

| | | | |
|---|---|---|---|
| 402,543 | 4/1989 | Roeske | 210/264 |
| 607,155 | 7/1898 | Bleakly et al. | 210/286 X |
| 789,968 | 5/1905 | Ernst | 210/286 X |
| 1,140,726 | 5/1915 | Warden | 210/286 X |
| 2,365,221 | 12/1944 | Shafor | 210/660 |
| 2,781,301 | 2/1957 | Payne | 422/188 X |
| 2,878,935 | 3/1959 | Magrath et al. | 210/738 |
| 3,127,247 | 3/1964 | Davis, Jr. | 422/188 |
| 3,298,527 | 1/1967 | Wright | 210/286 X |
| 4,197,287 | 4/1980 | Piasio et al. | 422/58 X |
| 4,412,866 | 11/1983 | Schoenrock et al. | 210/676 X |
| 4,511,476 | 4/1985 | Schoenrock | 210/768 |

Primary Examiner—Jill A. Johnston
Attorney, Agent, or Firm—J. Winslow Young

[57] ABSTRACT

An apparatus and method for providing a uniform flow profile for a liquid through a packed bed in a large diameter, low-pressure vessel. The liquid is distributed evenly across the top surface of the packed bed and directed through discrete flow regions through the packed bed. The flow regions are defined by flow straighteners which inhibit lateral flow of the liquid beyond the flow regions. The vessel includes a collector for removing the liquid after it has passed through the vessel.

5 Claims, 3 Drawing Sheets

APPARATUS AND METHOD FOR PROVIDING A UNIFORM FLOW PROFILE THROUGH LARGE DIAMETER, LOW-PRESSURE VESSELS

RELATED APPLICATIONS

This application is a continuation-in-part application of my copending application Ser. No. 07/267,848; filed Nov. 7, 1988 for METHOD AND APPARATUS FOR MAINTAINING UNIFORM PLUG FLOW IN PACKED COLUMNS (now abandoned) which was a continuation-in-part of Ser. No. 07/054,754; filed May 26, 1987 for METHOD AND APPARATUS FOR MAINTAINING UNIFORM PLUG FLOW IN PACKED COLUMNS (now abandoned) which was a continuation-in-part application of my original application Ser. No. 06/793,213; filed Oct. 31, 1985 for MAINTAINING UNIFORM PLUG FLOW IN PACKED COLUMNS (now abandoned).

BACKGROUND

1. Field of the Invention

This invention relates to large diameter, low pressure vessels and, more particularly, to a novel apparatus and method for providing a uniform flow profile through a large diameter, low pressure vessel.

2. The Prior Art

Numerous processes in the chemical industry require the passage of large volume liquid streams through loosely packed beds where certain reactions occur. Importantly, many of these liquid streams involve highly sensitive components that are adversely affected by extended exposure to the constituents of the packed beds. One method for carefully controlling the exposure or contact time is to divide the large stream into a plurality of smaller streams and direct each of these smaller streams into a separate, low-pressure, packed column where the inflow rates and residence times in the column can be precisely controlled.

Ideally, the liquid flowing through the packing flows downwardly with a uniform "front" when viewed in cross section across the column. This means that at any given point along the length of the column the liquid "front" in that particular cross section of the column will be uniform in composition. The term "plug flow" has been used to describe the movement of this hypothetical "front" of liquid through the column. Clearly, of course, the term "plug flow" is somewhat of a misnomer in that it appears to imply that a "plug" of liquid flows through the column whereas in reality, the column operates under steady state conditions so that the "front" at any given point along the length of the column is uniform throughout the cross sectional area of the column although the composition with each "front" will vary along the length of the column according to the control parameters imposed on the column.

This is an important distinction for identifying the unique features of the novel apparatus and method of this invention to distinguish it over the various devices of the prior art. One series of prior art technology involves high pressure separation in small laboratory columns and reactors typically used for analytical liquid and gas chromatography. These columns may contain sorbent material coated on the interior surface area or columns which are tightly packed with finely ground ion exchange material. These columns impose a high pressure drop on the liquid passing through the column. Others include a bundle of fins radiating from the outside wall toward the center, the fins being used to act as radiators for the purpose of temperature control. The fins also impose frictional resistance and turbulence on the liquid passing through the column and thereby achieve uniform cross sectional distribution and to provide large contact area at pressures exceeding 200 psi to over 2,000 psi. To meet these objectives the interior fins must be in close proximity to each other with a separation of only a few millimeters. Small analytical laboratory columns with such fin members are typically less than one inch in diameter. Such techniques are not applicable to large diameter, commercial type columns and reactors where design limitations and costs would prohibit the use of fins in close proximity to each other and restrict operation to relatively low pressures below 200 psi and where the sorbent packing material which represents a major part of the total costs would be damaged by continuous, long term high pressure operation.

Wright (U.S. Pat. No. 3,298,527) discloses a chromatographic flow column wherein inwardly directed longitudinal fin members extend radially from the outer wall of the column toward the center of the column. These fins are used to present frictional surfaces throughout the cross section of the column. The fins are also used as radiators to facilitate temperature control in the column. The heat is supplied to the exterior column wall surface where the fins conduct the heat into the interior of the column. The moving phase travelling through an unpacked column encounters flow resistance not only at the inner periphery of the column wall but also at the surfaces of the fin members as well. Wright teaches the distribution of the fin members evenly throughout the cross section of the column. Conversely, in a packed column, when the moving phase travels through the column, a greater resistance to flow is offered at the interior portions of the granular packing material than by the packing located adjacent the column wall and adjacent the fin walls. However, since the surfaces of the fins of Wright are distributed throughout the cross section of the column, the forces tending to produce differences in flow velocity are thereby more uniformly arranged throughout the cross section of the tube, and a relatively uniform flow velocity can thus be attained. (See column 3, lines 55–65).

In summary, the reference of Wright teaches the use of uniformly distributed, inwardly oriented, longitudinal fins to provide increased flow uniformity through the frictional resistance to flow contributed by the fins. The foregoing frictional resistance to flow contributed by the fins can be accentuated by producing the column in segments and, prior to joining the segments end-to-end into a column, rotating each segment relative to the adjacent segment thus producing an offset between adjacent fins. The fins of Wright are also used to carry externally applied heat into the interior of the column.

Other references include that of Warden (U.S. Pat. No. 1,140,726) which discloses a filter wherein the filter media is disposed in spaced, concentric annular walls through which the liquid to be filtered passes in lateral flow through each concentric filter sequentially.

The reference of Piasio (U.S. Pat. No. 4,197,287) discloses a laboratory diagnostic device wherein one or more solid phase matrices are affixed to longitudinal fins mounted in a test tube. The fins provide the solid phase matrix with an increased surface area relative that which would otherwise be available if only the inner wall of the test tube were coated with the solid phase matrix. Accordingly, the surface area to volume ratio is substantially increased thereby providing a corresponding increase in the overall reaction rate for the diagnostic technique.

Bleakly (U.S. Pat. No. 607,155) discloses a filter for filtering the water of streams, lakes, etc. The filter includes a reverse flow system for cleaning the filter bed.

Shafor (U.S. Pat. No. 2,365,221) discloses a reactor vessel for conducting ionic exchange operations wherein a floating distributor plate is supported on the top surface of the ion exchange resin bed. The distributor plate uniformly distributes the liquid undergoing treatment in the resin bed across the top surface of the resin bed.

Numerous filters, distillation columns, reactor vessels, and chemical processing strategies are known throughout the industry. However, what is needed is an apparatus for providing a uniform flow profile through a large diameter, low pressure vessel. It would also be an advancement in the art to provide improvements in methods for passing a liquid stream through a large diameter, low-pressure vessel wherein the liquid passes with a uniform frontal passage with minimal lateral movement of the liquid within the theoretical front. Such a novel apparatus and method is disclosed and claimed herein.

BRIEF SUMMARY AND OBJECTS OF THE INVENTION

This invention relates to a novel apparatus and method for providing a uniform flow profile in a liquid passing through a large diameter, low-pressure vessel, the vessel including a packed bed. The cross sectional area of the vessel is segregated by longitudinal dividers or more accurately, flow straighteners, into flow zones through which the liquid flows, the flow straighteners preventing lateral flow between the flow zones. The ratio of the cross sectional area of the flow zones is significantly reduced in order to minimize the drag coefficient imparted to the liquid by the side walls of the flow straighteners versus the total area of flow through the packed bed available to the liquid.

It is, therefore, a primary object of this invention to provide improvements in apparatus for assuring uniformity of the flow profile of a liquid through a packed bed in a large diameter, low-pressure vessel.

Another object of this invention is to provide improvements in the method for assuring uniformity of the flow profile of a liquid through a packed bed in a large diameter, low-pressure vessel.

Another object of this invention is to provide a large diameter, low-pressure vessel having a packed bed with flow straighteners which limit the lateral migration of liquid within the vessel thereby assuring a uniform flow profile within the liquid passing through the vessel.

These and other objects and features of the present invention will become more readily apparent from the following description and accompanying drawing taken in conjunction with the appended claims.

DETAILED DESCRIPTION OF THE PREFERRED EMBODIMENT

Figure 1:
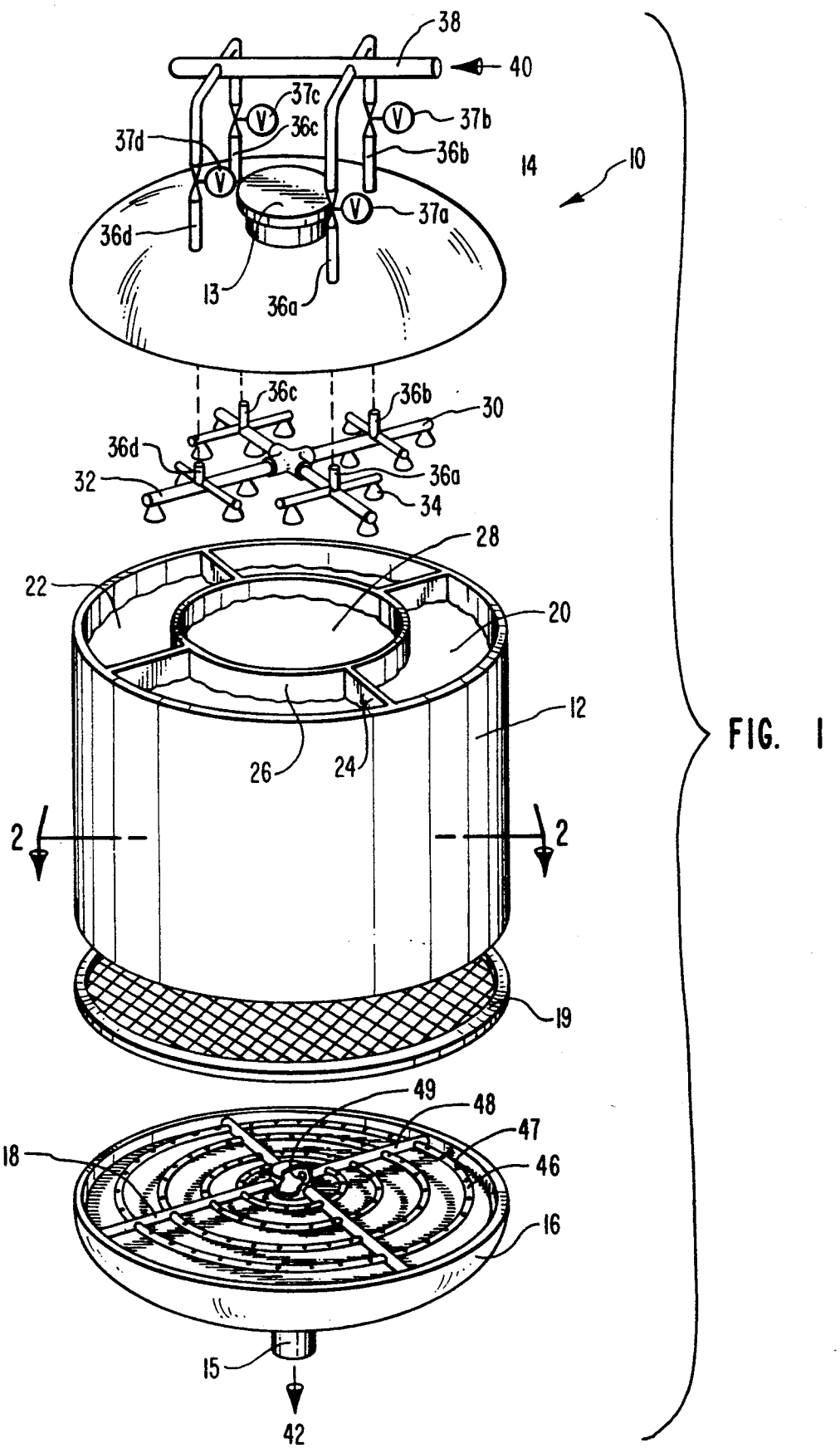
FIG. 1 is an exploded perspective view of a first preferred embodiment of a large diameter, low-pressure vessel having a packed bed with the novel flow straightener apparatus of this invention therein.

The invention is best understood by reference to the following description taken in conjunction with the drawing wherein like parts are designated with like numerals throughout.

General Discussion

Numerous chemical processes involve the passage of a liquid stream through a packed bed where certain chemical reactions occur. The packed bed can include any suitable packing material and is usually randomly dispersed with a loosely packed density throughout the packed bed. The random dispersion of the packing material generally assures that there will be maximum exposure of the packing material to the liquid stream with minimal channeling of the liquid through the packed bed. The packing material, per se, can be selected from a wide variety of materials ranging from fibrous packing material to discrete elements, each having a uniform size and shape but randomly dispersed in the packed bed. Some common shapes include hollow cylinders, split rings, or hollow cylinders with one or more dividers oriented longitudinally in the hollow cylinders, to name a few.

The processing of a liquid stream through a packed bed can present unique problems if the process parameters are relatively sensitive to variations. For example, if the packed bed acts as the mechanical support system for an enzymatic catalyst the total residence time of the liquid stream in the packed bed can be critical. Factors that affect this residence time include channelling of the liquid through the packed bed and lateral flow of the liquid stream in the packed bed versus the overall longitudinal flow. Advantageously, channelling is substantially eliminated in a packed bed having the packing loosely and randomly packed therein.

Lateral flow becomes especially critical particularly in large diameter vessels. Large diameter vessels are defined generally as those with a diameter greater than about five feet (1.5 meters) and are commonly accepted throughout the chemical processing industry particularly for handling of large volumes of liquids at low pressures. The alternative is to "gang" in parallel a plurality of processing vessels each of which is fed off a common header. However, the capital costs for such a processing scheme would render many chemical processing strategies uneconomical. Instead, large diameter, low-pressure vessels are used and the fluctuations in product quality resulting from the foregoing lateral flow phenomena are largely ignored due to the capital costs otherwise required.

Customarily, most processing vessels, even those used in low-pressure applications, are cylindrical in cross section and are oriented with the axis of the cylinder in the vertical position. The incoming liquid stream is distributed uniformly across the upper surface of the packed bed and allowed to flow downwardly through the packed bed. My invention utilizes flow straighteners within the packed bed itself for limiting the lateral migration of the liquid through the packed bed. These flow straighteners create flow regions or flow zones, each of which is defined by the particular set of flow straighteners. The flow straighteners of my invention become important as the cross sectional area of the vessel increases because of the difficulty in maintaining uniform longitudinal flow increases with the increasing cross sectional area. This means that the containment vessel suitable for the practice of this invention can be of a diameter so large as to be totally unfeasible if used according to the teachings of the prior art.

Clearly, other shapes, orientations and flow strategies can be used for particular processing schemes although the basic principles of this invention are readily applicable to these shapes, orientations, and flow strategies. Further, with the large diameter, high volume, packed bed vessel of this invention wherein the vessel includes flow straighteners in the packed bed, the wall effects from the separators are negligible. In the absence of flow straighteners it would be nearly impossible to maintain a uniform front within the longitudinal flow path of the liquid. Accordingly, it has become the conventional practice to limit the diameter of the vessel to that which will maintain the flow profile within acceptable limits, given the parameters of the particular processing strategy in question.

Detailed Description

Referring now to FIG. 1, the novel apparatus of this invention for providing a uniform flow profile through a large diameter, low-pressure vessel is shown generally at 10 and includes a large diameter, low-pressure vessel 12, a header 14, and a collector 16, each of which will be described in more detail hereinafter. Vessel 12 is segregated into a plurality of longitudinal flow zones 28 and 22 by a diametrally reduced cylinder 26 which acts as a cylindrical flow straightener and a series of longitudinal flow straighteners 24. Cylindrical section 26 is located coaxially in vessel 12 to create flow zone 28 with the annular space surrounding cylindrical section 26 being segregated into four flow zones 22 by radially oriented flow straighteners 24 extending between cylindrical section 26 and the internal wall of vessel 12. Flow straighteners 24 are joined between cylindrical section 26 and vessel 12 to provide mechanical support for cylindrical section 26. Each of flow zones 28 and 22 is loosely packed with a packing 20 through which the liquid 40 is passed during its passage through vessel 12. A screen 19 is supported on a grid 17 above a collector plate 18 in collector 16 and serves as a retainer for keeping packing 20 in each of flow zones 28 and 22.

Header 14 encloses the top of vessel 12 and contains a distributor 30 through which liquid stream 40 is spread uniformly over the top surface of packing 20 in each of flow zones 28 and 22. In particular, distributor 30 is configured with a plurality of feeder pipes 32 from which diffusers 34 depend downwardly. A 6 plurality of feed lines 36a-36d pass through header 14 and connect distributor 30 with incoming liquid 40 in product line 38. Valves 37a-37d in each feed line 36a-36d, respectively, are used to selectively regulate the amounts of liquid 40 delivered by feed lines 36a-36d to distributor 30 from product line 38.

An access port 13 in header 14 provides access into vessel 12 for purposes of inspection, maintenance, and even replacement of packing 20. This feature is a common feature for any large diameter vessel.

Collector 16 supports collector plate 18 which serves as a catchment to receive a liquid stream 42 after it has passed through packed bed 20. In particular, grid 17 is supported by collector plate 18 across the upper portion of collector 16 and includes a plurality of concentric collector tubes 46 connected to a plurality of radially oriented drain lines 48. Collector tubes 46 include a plurality of perforations 47 oriented toward collector plate 18 and through which liquid 42 is withdrawn from collector 16. Drain lines 48 feed directly through an outlet 49 into a centrally located drain column 15 to allow the outflow of liquid 42 from collector 16.

Figure 2:
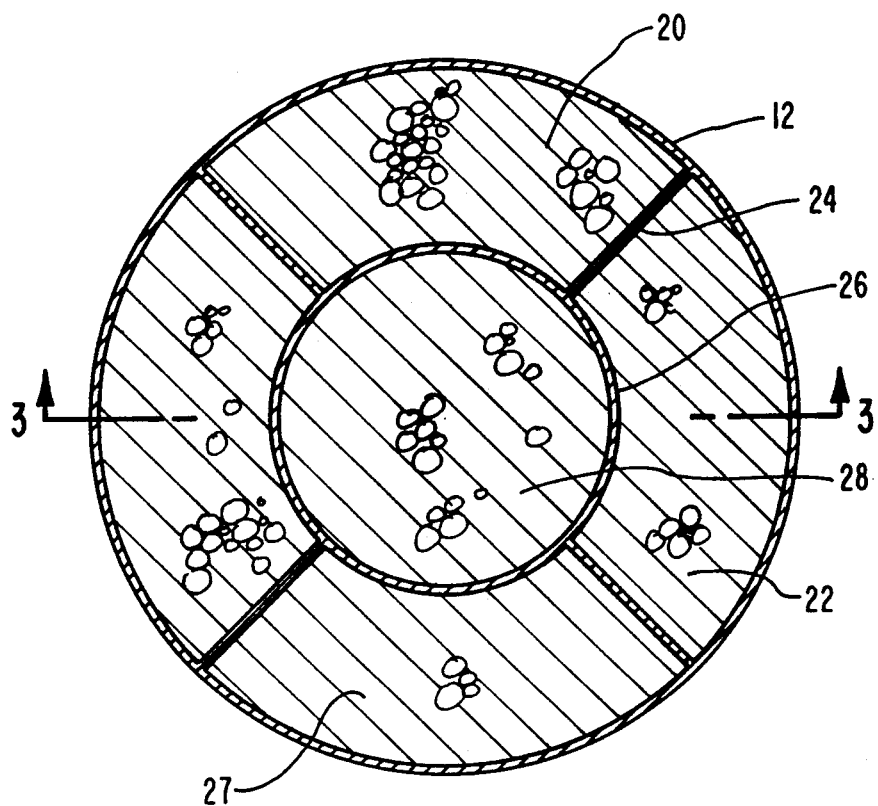
FIG. 2 is a cross sectional view taken along lines 2—2 of FIG. 1.

With specific reference to FIG. 2, the arrangement of cylindrical section 26 and flow straighteners 24 is shown more clearly. In particular, cylindrical section 26 is shown concentric within vessel 12 while flow straighteners 24 are arrayed radially in the annular space between cylindrical section 26 and the wall of vessel 12. Cylindrical section 26 creates cylindrical flow zone 28 whereas the combination of cylindrical section 26, flow straighteners 24, and the wall of vessel 12 defines flow zones 22 which can be described generally as being segmented annular flow zones.

Figure 3:
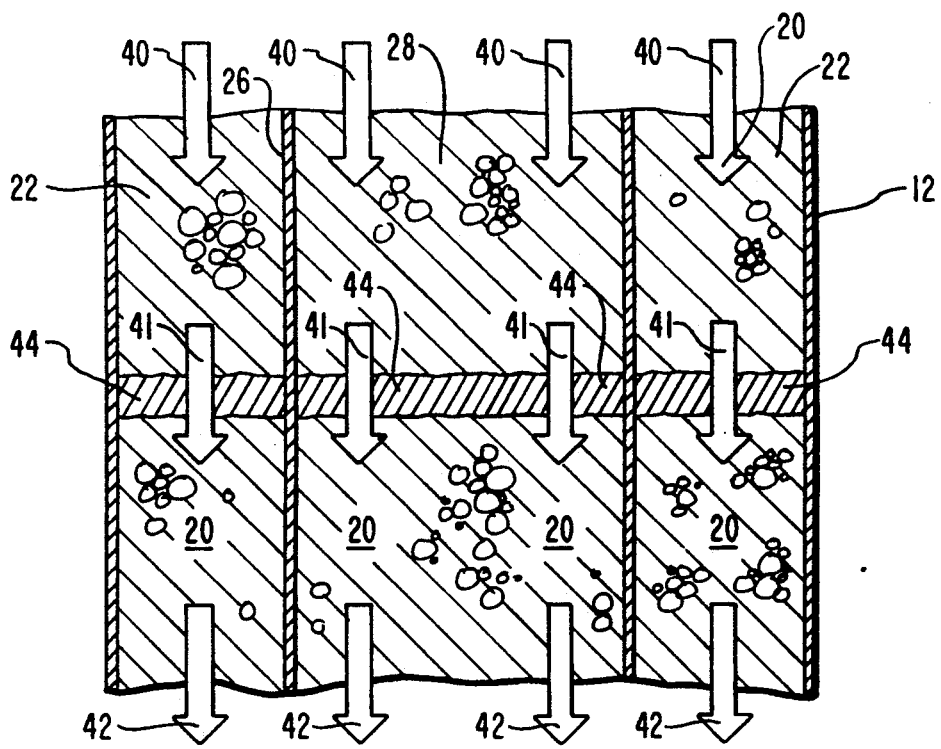
FIG. 3 is an enlarged, fragmentary cross sectional view taken along lines 3—3 of FIG. 1 to illustrate schematically the flow profile through the packed bed inside the large diameter, low-pressure vessel wherein are placed the novel flow straighteners of this invention.

Referring now specifically to FIG. 3, the passage of liquid 40 through packing 20 in flow zones 28 and 22 is illustrated schematically by an upper flow arrow 40 representing incoming liquid and a lower flow arrow 42 representing the liquid stream departing flow zones 28 and 22. The liquid in transition through flow zones 28 and 22 is illustrated schematically by flow arrow 41 superimposed across a horizontally uniform flow profile illustrated schematically as flow profile 44. Clearly, flow profile 44, as such, does not exist as a unitary body that could be isolated from flow zones 28 and 22. However, flow profile 44 does clearly set forth the novel feature of this invention in that the creation of flow zones 28 and 22 by the use of cylindrical section 26 and flow straighteners 24, respectively, does substantially inhibit the lateral migration of liquid stream 41 which would otherwise result in flow profile 44 being nonuniform in its cross section, as shown. In the absence of flow straighteners 24 and cylindrical section 26, flow profile 44 would be substantially distorted (not shown) such that one or more sections of vessel 12 would experience a higher flow profile while other sections would experience a substantially diminished flow profile.

Clearly, a nonuniform flow profile through vessel 12 is to be avoided through all reasonable efforts. It is for this reason that I have made this novel invention wherein I substantially eliminate lateral flow within vessel 12 by the incorporating cylindrical section 26 and flow straighteners 24 which combine to create flow zones 28 and 22, respectively, within vessel 12. This means that regardless of the position in flow zones 28 and 22 that one examines flow profile 44 it will be found that flow profile 44 is essentially uniform across its horizontal plane in each respective flow zone. This feature is known in the art of chemical processing as "plug flow" although I have chosen not to use this term in describing my invention since it may be interpreted by others to imply some form of cyclic change in flow profile 44 as it passes through flow zones 28 and 22 whereas flow profile 44 is clearly uniform at any given time and at any given position within flow zones 28 and 22.

Figure 4:
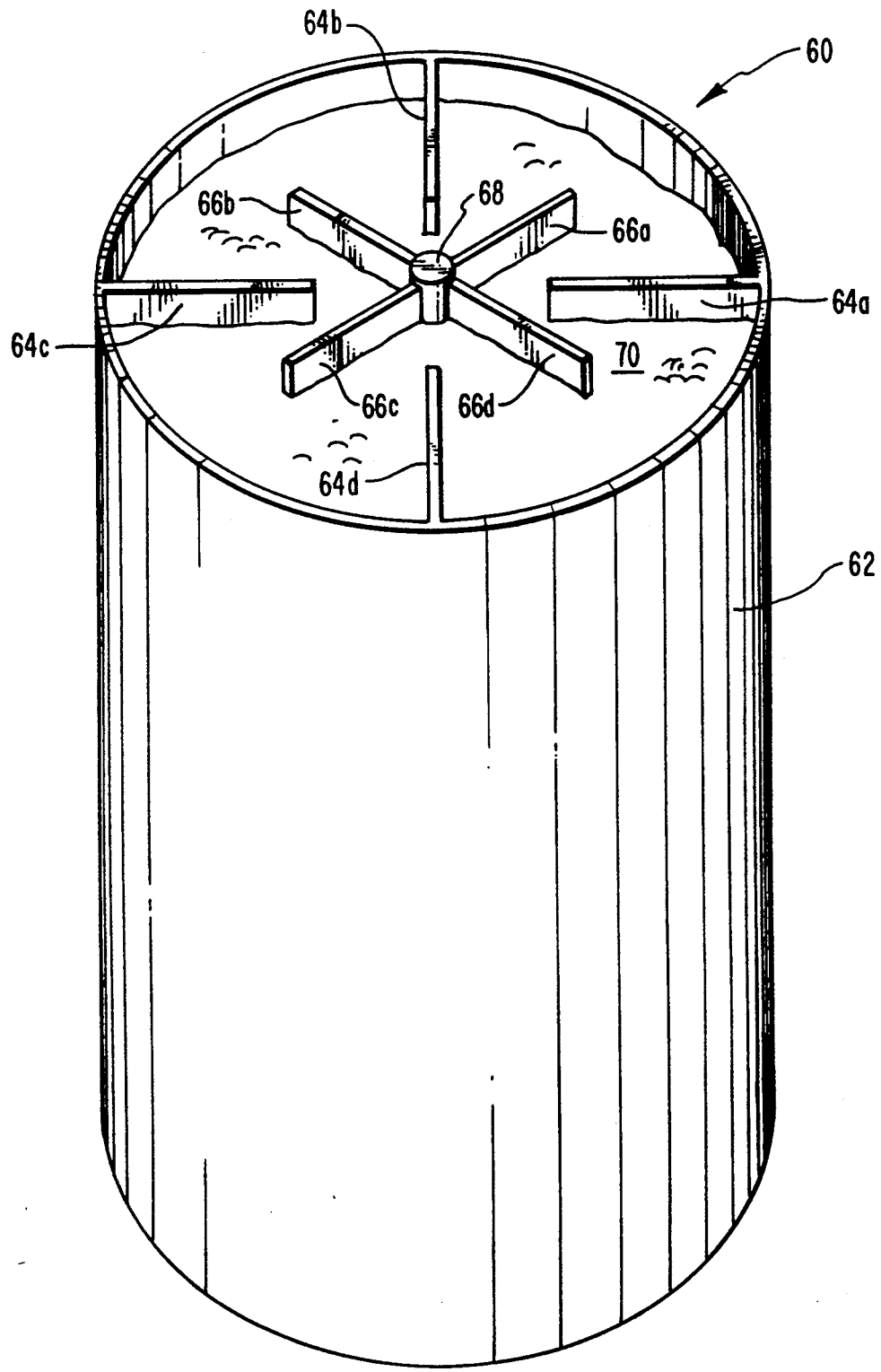
FIG. 4 is a perspective view of a second preferred embodiment of the novel flow straightener apparatus of this invention shown in the environment of a packed bed in a large diameter, low-pressure vessel.

Referring now to FIG. 4, a second preferred embodiment of the novel apparatus for providing a uniform flow profile in a large diameter, low-pressure vessel is shown generally at 60 and includes a vessel 62 having a packed bed 70 therein. Vessel 62 and packed bed 70 are in all aspects identical to vessel 12 and packed bed 20, respectively, (FIGS. 1-3), the only exception being in the configuration of the flow straightening devices in packed bed 70 as will be discussed more fully hereinafter. The rest of the features relating to header 14 and collector 16 (FIG. 1) are identical so that no additional discussion of these elements will be necessary.

Vessel 62 includes a plurality of longitudinal, radial flow straighteners 66, individually designated herein as radial flow straighteners 66a-66d, extending radially outwardly from a center post 68. Center post 68 is coaxial with vessel 62. Each of radial flow straighteners 66a-66d is uniformly spaced in its angular relationship. The four flow straighteners shown are each offset 90 degrees from the adjacent flow straightener. Importantly, the radial distance that each of radial flow straighteners 66a-66d extends into packed bed 70 is less than the radial distance from center post 68 to the wall of vessel 62. Preferably, this radial distance of radial flow straighteners 66 is incrementally greater than half the radius of vessel 62.

Radial flow straighteners 66 partially segregate packed bed 70 longitudinally into four equal quadrants which are bisected by four diametral flow straighteners 64, each of which is designated herein as diametral flow straighteners 64a-64d. Diametral flow straighteners 64 extend inwardly from the wall of vessel 62 along the diameter of vessel 62 and for a distance incrementally greater than half the radius of vessel 62. This feature means that there is a certain degree of overlap between the inward extension of diametral flow straighteners 64 and the outward extension of radial flow straighteners 66 so that between them they create flow regions through packed bed 70. These flow regions are essentially identical to flow zones 28 and 22 (FIGS. 1-3) with the exception that they are not fully enclosed on all sides. However, radial flow straighteners 66 and diametral flow straighteners 64 cooperate in directing liquid 40 (FIGS. 1-3) through packed bed 70 and significantly limiting the degree of lateral flow therein.

The Method

Referring again to FIGS. 1-3, the method of this invention involves obtaining a large diameter, low-pressure vessel 12 and placing a cylindrical section 26 and a plurality of flow straighteners 24, therein to create flow zones 28 and 22, respectively. Cylindrical section 26 is mounted coaxially in vessel 12 and is formed with a diametrally reduced diameter inside vessel 12 so as to create flow zone 28 and an annular space with vessel 12 which is segregated into flow zones 22 by mounting flow straighteners 24 radially and equidistantly within the resulting annular space.

Flow zones 28 and 22 are filled with the packing of packed bed 20 and are configured with their respective axes parallel to the axis of vessel 12. Further, the cross sectional area of flow zone 28 is substantially equal to the cross sectional area of each of flow zones 22. Great care is taken in creating flow zones 28 and 22 particularly with respect to the relative sizes of the same since it is undesirable to introduce relatively large wall effects on incoming liquid 40 by the size, number and relative placement of cylindrical section 26 and flow straighteners 24. This is important to preclude the flow straightening effect of cylindrical section 26 and flow straighteners 24 from adversely interfering with the uniformity of flow profile 44.

With the creation of flow zones 28 and 22, they are ready to receive liquid 40 dispersed thereon. Distributor 30 uniformly dispenses liquid 40 across the upper surface of packed bed 20 where it is directed downwardly through flow zones 28 and 22. Advantageously, since flow zones 28 and 22 are defined by the respective boundaries created by cylindrical section 26, flow straighteners 24, and vessel 12, the lateral migration of liquid 41 as it passes through packed bed 20 is restricted to the particular flow zone through which it is passing.

The emerging liquid 42 passes through screen 19 and is collected on collector plate 18 where it is then removed through perforations 47 in concentric, collector pipes 46. Collector pipes 46 feed into drain lines 48 which in turn pass into drain pipe 15.

In summary, liquid 40 is processed as liquid 41 in packed bed 20 to become liquid 42. Importantly, flow zones 28 and 22 confine liquid 41 into the respective flow zones thereby substantially eliminating lateral flow so as to provide uniformity to flow profile 44. In this manner, liquid 40 can be successfully treated in a packed bed 20 contained within a large diameter, low-pressure vessel 12.

Referring now to FIG. 4, packed bed 70 is segregated into general flow regions by radial flow straighteners 66 and diametral flow straighteners 64. These flow regions are not defined on all sides by a flow straightener but are sufficiently defined so as to significantly result in having a uniform flow profile 44 (FIG. 3) therein which is a primary object of this invention.

Importantly, the number of flow straighteners versus the cross sectional area of vessel 72 (or vessel 12, FIGS. 1-3) is carefully limited so as to minimize the frictional resistance to flow contributed by the wall surfaces of the respective flow straighteners versus the total resistance to flow encountered in packed bed 70 (see also packed bed 12, FIGS. 1-3).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for providing a uniform flow profile for liquid passing through a packed bed in a large diameter, low-pressure vessel comprising:

a large diameter vessel having a diameter greater than about 1.5 meters;

a coaxial, center post in said vessel;

a packed bed in said vessel;

liquid distribution means in said vessel above said packed bed for distributing a liquid uniformly across an upper surface of said packed bed;

flow straightener means in said packed bed comprising a a first set of longitudinal baffles and a second set of longitudinal baffles in said packed bed, said first set of longitudinal baffles extending radially outwardly from said center post while being uniformly spaced about said center post and extending incrementally beyond a midpoint between said center post and said vessel, said second set of longitudinal baffles being spaced uniformly around said vessel and extending inwardly toward said center post incrementally beyond a midpoint between said vessel and said center post, said first set and said second set of longitudinal baffles forming flow zones in said packed bed with said liquid flowing through said flow zones, said first set and said second set of longitudinal baffles inhibiting lateral flow of said liquid within said packed bed between said flow zones, the number of longitudinal baffles limiting differences between the frictional resistance to flow imparted to said liquid by the wall surface area of said longitudinal baffles when compared to the total cross sectional area of flow available to said liquid; and collector means below said packed bed for collecting and removing said liquid after it has passed through said packed bed.

2. The apparatus defined in claim 1 wherein said flow zones comprise flow zones having cross sectional areas that are substantially equal.

3. An apparatus for providing a uniform flow profile for liquid passing through a packed bed in a large diameter, low-pressure vessel comprising:

a large diameter vessel having a diameter greater than about 1.5 meters and a vertical axis;

a packed bed in said vessel;

liquid distribution means above said packed bed in said vessel for delivering a liquid uniformly across a top surface of said packed bed;

a first flow zone in said vessel comprising a concentric flow zone formed with a cylindrical sidewall in spaced relationship to said vessel;

a plurality of second flow zones formed by a plurality of radial flow straighteners in said large diameter vessel, said radial flow straighteners forming a plurality of flow regions in said packed bed between said concentric flow zone and said vessel, each of said flow regions having an axis parallel to said vertical axis of said vessel, the number of flow straighteners limiting differences between the frictional resistance to flow encountered by said liquid in said packed bed and the wall surface frictional resistance to flow contributed by wall surfaces of said flow straighteners when compared to the total resistance to flow encountered by said liquid in said packed bed; and collector means in said vessel below said packed bed for collecting liquid passing through said flow regions.

4. The apparatus defined in claim 3 wherein said first flow zone comprises a first cross sectional area and each of said second flow zones comprises a second cross sectional area, said first cross sectional area being approximately equal to said second cross sectional area.

5. A method for providing for a uniform flow profile of a liquid through a packed bed in a large diameter, low-pressure vessel comprising:

obtaining a large diameter vessel, said vessel having a diameter greater than about 1.5 meters, and orienting said vessel with its axis in a vertical orientation;

selecting a center post for said vessel and mounting said center post coaxially in said vessel;

placing a packed bed in said vessel;

preparing a plurality of longitudinal baffles for said vessel, said longitudinal baffles having a length generally corresponding to said packed bed, said longitudinal baffles segregating said packed bed into a plurality of flow regions, the axis of each flow region being parallel to said axis of said vessel, limiting the number of said longitudinal baffles to minimize wall surface frictional resistance to flow contributed by wall surfaces of said longitudinal baffles versus total resistance to flow of said liquid in said packed bed, said longitudinal baffles comprising a first set of longitudinal baffles and a second set of longitudinal baffles, said first set of longitudinal baffles extending outwardly from said center post and uniformly spaced about said center post, said second set of longitudinal baffles extending inwardly from the wall of said vessel with each of said second set of longitudinal baffles flow region formed by said first set of longitudinal baffles, each of said longitudinal baffles extending into said packed bed incrementally beyond a midpoint between said center post and said vessel;

distributing said liquid uniformly across said packed bed;

providing a uniform flow profile of said liquid through said packed bed by limiting lateral flow of said liquid to said flow zones with said longitudinal baffles; and collecting said liquid after passing through said packed bed.

* * * * *